US00PP18186P2

(12) United States Plant Patent
Sanders

(10) Patent No.: US PP18,186 P2
(45) Date of Patent: Nov. 6, 2007

(54) ***AGERATUM* PLANT NAMED 'AGPATBICPULI'**

(50) Latin Name: *Ageratum houstonianum*
Varietal Denomination: Agpatbicpuli

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/436,743

(22) Filed: May 18, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—S. B. McCormick-Ewoldt
(74) *Attorney, Agent, or Firm*—Bruce Vrana

(57) ABSTRACT

A new *Ageratum* plant named 'Agpatbicpuli' characterized by its large, deep violet flowers, early flowering, strongly branched plant habit and vigorous growth.

1 Drawing Sheet

Latin name of the genus and species of the plant claimed: *Ageratum houstonianum.*

Varietal denomination: 'Agpatbicpuli'.

BACKGROUND OF THE NEW PLANT

The present invention comprises a new and distinct cultivar of *Ageratum,* botanically known as *Ageratum houstonianum.*

The new cultivar is propagated from cuttings resulting from the cross of 'W 73-2' as female parent and 'Agmontis' as male parent. This cross was made in September 2001. 'W 73-2' is not commercially available and is not patented. 'Agmontis' is commercially available and is patented as U.S. Plant Pat. No. 15,301.

As a result of this cross the present cultivar was selected in September 2002 in Enkhuizen, Netherlands and has been repeatedly asexually reproduced by cuttings in Enkhuizen, Netherlands. The present cultivar was tested in Enkhuizen, Netherlands, in Gilroy, USA, and in Sarrians, France over a three year period. The distinctive characteristics of this new *Ageratum* are stable and reproduced true to type in successive generations of asexual reproduction. It takes 6 to 8 weeks to produce a finished plant, depending on the temperature.

This new *Ageratum* plant is an annual in most climatical zones in the US, only in zones 9 and 10 it is a perennial plant.

SUMMARY OF THE INVENTION

The following traits have been repeatedly observed and are determined to be the unique characteristics of 'Agpatbicpuli.' These characteristics in combination distinguish 'Agpatbicpuli' as a new and distinct *Ageratum* cultivar:

1. Vigorous, upright and mounded growth habit
2. Freely branching habit
3. Freely flowering habit with large capitula in compound umbels
4. Large, deep violet capitula on green colored leaves Plants of the new *Ageratum* differ primarily from the plants of the female parent selection in the following characteristics:

Plants of the new *Ageratum* have purple and violet bicolored capitula whereas plants of the female parent selection have purple capitula.

Plants of the new *Ageratum* differ primarily from the male plant selection in the following characteristics:

Plants of the new *Ageratum* have purple and violet bicolored capitula whereas plants of the female parent selection have purple capitula.

DESCRIPTION OF THE DRAWING

This new *Ageratum* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new *Ageratum.* The data which defines these characteristics were collected from asexual reproductions carried out in Enkhuizen, Netherlands. The plant history was taken on 20 week old plants, blossomed under natural light in the field.

Color readings were taken in the laboratory under ambient light. Color references are primarily to The R.H.S. Colour Chart of The Royal Horticultural Society of London.

TABLE 1

Differences between the new cultivar 'Agpatbicpuli' and a similar cultivar

| | 'Agpatbicpuli' | 'Agmontis' (U.S. Plant Patent No. 15,301) |
|---|---|---|
| Flower size | Large | Small |
| Flower color | Deep purple flowers with light violet pistils | Deep purple flowers with violet pistils |
| Leaf size | Medium | Small |

The plant:
*Classification.*—Botanical: *Ageratum houstonianum.*
*Growth habit.*—Ascending, well branched.
*Plant height.*—21–23 cm.
*Spreading area of plant.*—40–50 cm.
*Growth rate.*—Compact, vigorous.
*Strength.*—Very good.
*Branching character.*—Freely branching and lateral branching at every node.
*Blooming period.*—Year round.

The stem:
*Stem length.*—21–28 cm.
*Diameter.*—3 mm.
*Shape.*—Round.
*Color.*—RHS 145C.
*Anthocyan pigmentation.*—166A where present.
*Length of internode.*—19–36 mm, depending on the light where the plant is propagated.
*Pubescence.*—Slightly pubescent.

The foliage:
*Phyllotaxis.*—Opposite, decussate.
*Shape of blade.*—Ovate.
*Texture.*—Upper side: Slightly pubescent. Lower side: Slightly pubescent.
*Venation.*—Reticulate.
*Leaf margin.*—Serrate.
*Leaf base.*—Cordate.
*Leaf apex.*—Acute.
*Length.*—20–26 mm.
*Width.*—20–23 mm.
*Color.*—Upper side: Dark green RHS 137A. Lower side: Medium green RHS 138B.
*Pubescence.*—Some pubescence is present.
*Length of petiole.*—5–10 mm.
*Diameter of petiole.*—2–3 mm.
*Color of petiole.*—RHS 139D Light green.
*Petiole surface texture.*—Slightly pubescent.

Inflorescence:
*Inflorescence.*—Compound umbel of capitula.
*Number of inflorescence per plant.*—80–110.
*Umbel width.*—3–3.5 cm.
*Umbel depth.*—1.5–1.8 cm.
*Length of peduncle.*—8–12 mm.
*Diameter of peduncle.*—2 mm.
*Color of peduncle.*—RHS 145B, Anthocyanin may be present 166A.
*Length of pedicel.*—6–8 mm.
*Diameter of pedicel.*—1 mm.
*Color of pedicel.*—RHS 145A.
*Number of capitula per inflorescence.*—7–10.
*Number of disc florets per capitulum.*—50–85.
*Capitulum in bud stage from the start.*—Round, flat capitulum, showing unopened florets.
*Number of ray florets.*—0.
*Shape of the corolla of the disc floret.*—Actinomorph.
*Number of lobes.*—5.
*Length of disc floret.*—3 mm.
*Diameter of disc floret.*—1.5 mm.
*Color of disc floret.*—Upper side: RHS N78B to N78C. Lower side: RHS N78C.
*Number of phyllaries per capitulum.*—34–36.
*Length of phyllaries.*—4 mm.
*Diameter of phyllaries.*—1 mm.
*Color of phyllaries.*—Upper side: RHS 143C with tip RHS N78A. Lower side: RHS 145D with tip RHS N77A.
*Diameter of capitulum at beginning of flowering.*—6–8 mm.
*Depth of capitulum.*—5–7 mm.
*Color of capitulum at beginning of flowering.*—RHS N78B.
*Diameter of capitulum at full flowering.*—8–9 mm.
*Color of capitulum at full flowering.*—RHS N87B.

Reproductive organs:
*Number of pistils.*—1.
*Shape of pistils.*—Style with two filliform branches.
*Length of stigma and style.*—7 mm.
*Color of stigma.*—RHS N87A.
*Inferior ovary.*—5 ribbed.
*Pappus.*—Short.
*Number of anthers.*—5, connate in a tube, filaments free.
*Shape of anthers.*—Ecalcarate.
*Pollen.*—A little pollen is present.
*Color of pollen.*—RHS N155A.
*Fragrance.*—No fragrance.
*Lastingness of the bloom.*—The capitula of one umbel open over a period of 3–4 weeks.
*Seedset.*—Has seedset.

Seed:
*Shape.*—Pentagonal.
*Length.*—2 mm.
*Diameter.*—0.8 mm.
*Color.*—RHS 202A.
*Pappus.*—Very short.

Roots:
*Type of roots.*—Fibrous. Roots start to grow on every part of the stem that contacts the soil, so not only at the nodes.

Physiological and ecological characteristics: Good tolerance to heat and cold, but no frost tolerance. Strong tolerance to pests and diseases.

What is claimed is:

1. A new and distinct cultivar of *Ageratum houstonianum* plant named 'Agpatbicpuli', as substantially illustrated and described herein.

* * * * *

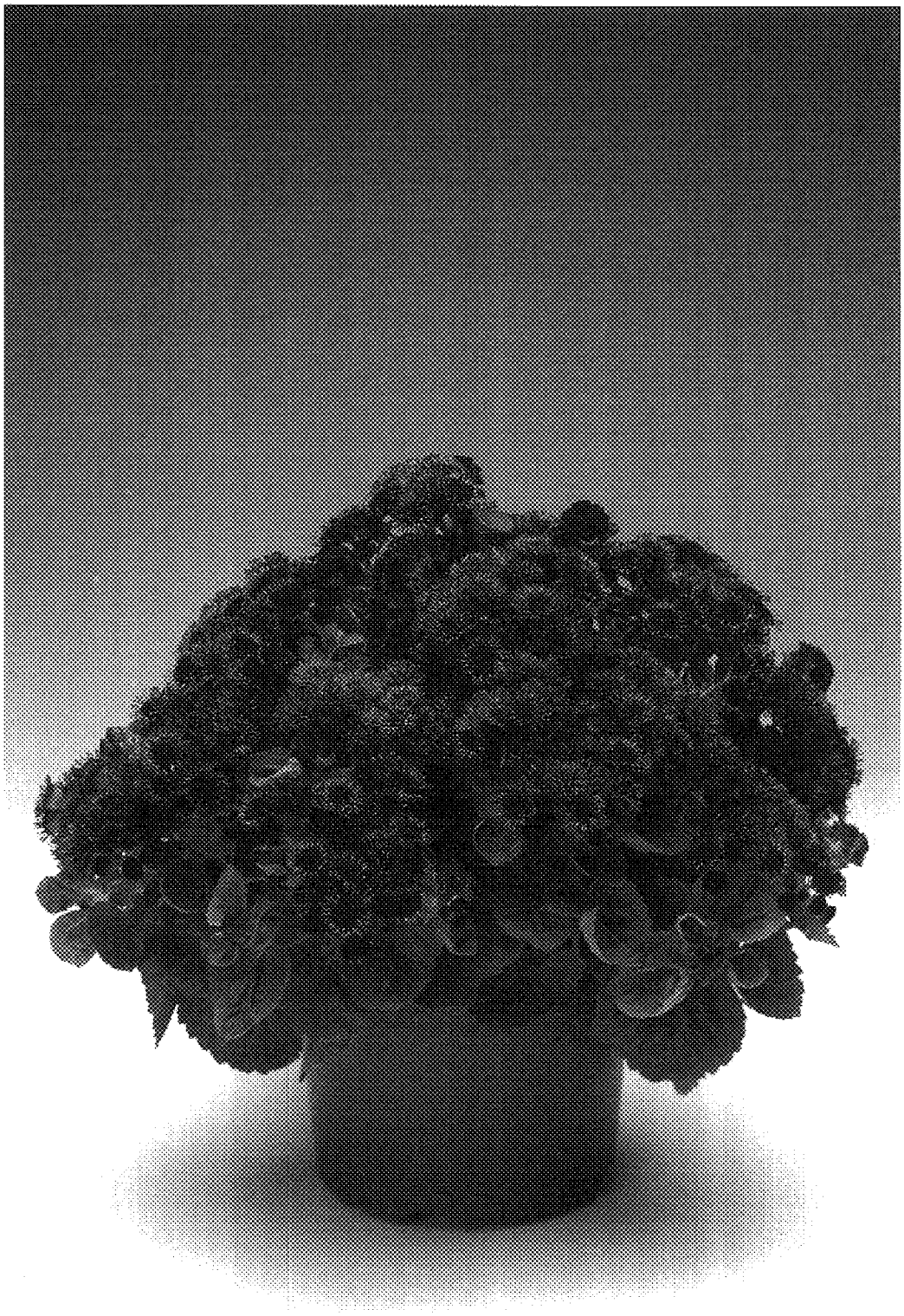

UNITED STATES PATENT AND TRADEMARK OFFICE

CERTIFICATE OF CORRECTION

PATENT NO. : PP 18,186 P2
APPLICATION NO. : 11/436743
DATED : November 6, 2007
INVENTOR(S) : Sanders It is certified that error appears in the above-identified patent and that said Letters Patent is hereby corrected as shown below:

At column 2, line 10, please delete "female parent" and insert therefor --male parent--

Signed and Sealed this

Twenty-seventh Day of May, 2008

JON W. DUDAS
*Director of the United States Patent and Trademark Office*